United States Patent [19]

Burri et al.

[11] Patent Number: 5,362,503
[45] Date of Patent: Nov. 8, 1994

[54] PROCESS FOR THE PRODUCTION OF DRIED FRUITS

[75] Inventors: Josef Burri, Epalinges; Pierre Nicod, Bottens, both of

[73] Assignee: Nestec S.A., Vevey, Switzerland

[21] Appl. No.: 977,594

[22] Filed: Nov. 17, 1992

[30] Foreign Application Priority Data

Dec. 13, 1991 [CH] Switzerland ............... 3697/91-6

[51] Int. Cl.$^5$ .............................................. A23B 7/10
[52] U.S. Cl. ................................ 426/50; 426/52; 426/640
[58] Field of Search .................. 426/49, 640, 50, 52

[56] References Cited

U.S. PATENT DOCUMENTS 3,615,687 10/1971 Mochizuki et al.
4,542,033 9/1985 Agarwala.
4,917,910 4/1990 Hsieh et al. ................... 426/102

FOREIGN PATENT DOCUMENTS 981523 1/1976 Canada.
0404543 12/1990 European Pat. Off.
1168181 7/1985 U.S.S.R.
9100022 1/1991 WIPO.

*Primary Examiner*—Donald E. Czaja
*Assistant Examiner*—Curtis E. Sherrer
*Attorney, Agent, or Firm*—Vogt & O'Donnell

[57] ABSTRACT

Dried fruits are treated by contacting and incubating them with a glycerol solution containing a carbohydrase enzyme in an amount of 0.05 to 0.5 parts enzyme by weight per 100 parts fruit at a temperature of from 40° C. to 60° C. for a time sufficient so that the fruit absorbs at least 10% by weight glycerol. The carbohydrase enzyme is inactivated and the incubated fruit is dried so that the fruit has a water activity of from 0.25 to 0.40.

15 Claims, No Drawings

PROCESS FOR THE PRODUCTION OF DRIED FRUITS

BACKGROUND OF THE INVENTION

This invention relates to a process for the production of dried fruits.

Certain food products of the ready-to-serve type, more particularly intended for breakfast, consist essentially of a mixture of cereals in the form of flakes and dried fruits either whole or in the form of cubes. The cereals used are generally wheat, corn and oats while the dried fruits may be apples, apricots, bananas, figs and grapes, for example.

One of the main characteristics of these food products is the crispy texture of the cereal flakes and the tenderness of the dried fruits. Accordingly, it is important that each of the constituents of the end product retain its own organoleptic qualities in storage up to the moment it is consumed.

Now, the crispiness of the cereal flakes and the tenderness of the dried fruits depend mainly on their water activity value (Aw). Thus, the cereal flakes have a crispy texture when their water activity is of the order of 0.15–0.25. When the water activity exceeds 0.35, the flakes lose their crispiness and become soft. Similarly, the dried fruits have a pleasant tenderness when their water activity is of the order of 0.50 to 0.55. When the water activity falls below 0.40, the dried fruits become hard.

When the end food product is produced and stored by mixing the cereal flakes and the dried fruits, a transfer of moisture can take place so that the dried fruits lose water to the cereal flakes. A balance is generally obtained around a water activity value of the end product of 0.25–0.40, at which the flakes are soft and the dried fruits are hard.

Now, it has already been proposed to treat the fruits with a humectant, such as glycerol, so that they retain a pleasant and tender texture for a water activity value below 0.50. To obtain good absorption of the humectant in the fruits, it is preferable to increase the permeability of their skin by pretreatment before they are steeped in the humectant.

Thus, it is known, for example from Canadian Patent No. 981,523, that the fruits can be subjected to a hot pretreatment with a weak acid and then to treatment with a humectant, such as a solution of sorbitol or glycerol, for about 15–24 hours so that the fruits absorb at least 3% humectant. The fruits thus treated are then dried to a dry matter content of 80 to 88%.

SUMMARY OF THE INVENTION

The problem addressed by the present invention was to provide a process for the production of dried fruits in which the step of pretreatment with a weak acid would be avoided.

Accordingly, the present invention provides a process in which dried fruits are contacted with a solution of glycerol containing 0.05–0.5 part carbohydrase enzymes per 100 parts fruits, the fruits are incubated in contact with the glycerol solution at a temperature of 40° to 60° C. until the fruits have absorbed at least 10% glycerol, the enzymes are inactivated and the fruits obtained are dried to a water activity of 0.25–0.40.

The use of a solution of glycerol containing carbohydrase enzymes enables the time required to prepare the dried fruits to be significantly reduced on the one hand, by eliminating the pretreatment step and, on the other hand, by reducing the incubation time of the fruits in the presence of the glycerol. This is because it appears that the use of a solution of glycerol containing carbohydrase enzymes enables the permeability of the skin of the treated fruits to be improved and hence, facilitates absorption of the glycerol by the fruits.

DETAILED DESCRIPTION OF THE INVENTION

In the rest of the present specification, parts and percentages are by weight unless otherwise stated.

In the process according to the invention, the dried fruits, for example either whole or precut into cubes and having a dry matter content of 85 to 88%, are contacted with a glycerol solution containing 0.05–0.5 part carbohydrase enzymes per 100 parts fruits to be treated. The glycerol solution may consist-either of pure glycerol or of an aqueous solution containing 80–90% glycerol. It preferably contains 0.1–0.4% carbohydrase enzymes. Any enzyme which allows correct diffusion of the glycerol into the fruits may be used as the source of carbohydrase enzymes. The enzyme used may be, for example, a cellulase, a mixed carbohydrase, a pectinase, a galactomannanase, a hemicellulase, or a mixture of these various enzymes. The glycerol solution containing the enzymes and the fruits are then contacted.

In a preferred embodiment, one part fruits is contacted with 1 to 2 parts glycerol solution. This may be done, for example, by steeping the fruits in the solution, preferably preheated to 40°–60° C., for 2 to 5 hours and preferably for 3 hours. In one preferred embodiment, the glycerol solution containing the enzymes may also be sprayed onto the fruits at a temperature of 40°–60° C. Spraying may also be carried out several times or in several steps. This embodiment provides for the use of a smaller quantity of glycerol (of the order of 70–80 ml per 100 g fruits) while promoting its absorption in the fruits.

The fruits are then incubated in contact with the glycerol solution at a temperature of 40°–60° C. until the fruits have absorbed at least 10% glycerol. For example, the fruits may be incubated in an oven for 2–5 hours at 40°–60° C.

The incubation time may be shortened by subjecting the fruits to a pretreatment before they are contacted with the glycerol solution. Thus, if the fruits are pretreated by immersion in water at 90°–100° C. for 2–4 minutes before they are contacted with the glycerol solution containing the enzymes, the incubation time at 40°–60° C. required to obtain a glycerol content of at least 10% is reduced to 1.5 h–2.5 h.

When the fruits have acquired the desired glycerol content, the enzymes are inactivated. This may be done, for example, by steeping the fruits in a glycerol solution at 75°–95° C. for 20–40 minutes. Inactivation in the glycerol reduces the migration of the sugars present in the fruits to the outside. The fruits thus obtained may be rapidly rinsed, for example in water, and are then dried, for example with hot air at 50°–70° C., for about 10–20 hours until a water activity of 0.25–0.40 and a dry matter content of the order of 88–92% are obtained.

EXAMPLES

The invention is illustrated in more detail by the following Examples.

Example 1

An 87% glycerol solution containing 0.1% of a carbohydrase is prepared. 100 g dried grapes having a dry matter content of 88% are steeped in 100 g of this solution heated beforehand to 50° C. The mixture is stirred to eliminate the air trapped at the surface of the grapes and is then incubated for 3 hours at 50° C.

After the incubation period, the grapes are steeped for 30 minutes in an 87% glycerol solution heated beforehand to 95° C. to inactivate the enzymes and are then rapidly rinsed with water to remove the glycerol present at their surface in order to facilitate their subsequent handling by minimizing the risks of adhesion and agglomeration. The grapes thus treated are then dried in a ventilated oven at 40° C. for about 15 hours with occasional turning. The dry grapes thus obtained have a dry matter content of 88–90%, a water activity of 0.29–0.32 and a glycerol content of 21.5%.

Example 2

An 87% glycerol solution containing 0.5% carbohydrase is prepared and heated to 50° C. This solution is sprayed onto dried grapes to moisten them as thoroughly as possible. The grapes are then spread over an aluminium foil and placed in an oven at 50° C. where they are left to incubate for 3 hours. During this 3 hour incubation period, the spraying step is repeated twice. After the incubation period, the grapes are steeped for 30 minutes in an 87% glycerol solution heated beforehand to 95° C. to inactivate the enzymes and are then rapidly rinsed with water to remove the glycerol present at their surface in order to facilitate their subsequent handling by minimizing the risks of adhesion and agglomeration. The grapes thus treated are then dried in a ventilated oven at 40° C. for about 15 hours with occasional turning. The dry grapes thus obtained have a dry matter content of 88–90%, a water activity of 0.29–0.32 and a glycerol content of 18.2%.

Example 3

Dried grapes having a dry matter content of 88% are steeped in hot water at 90°–100° C. for 3 minutes to tenderize their skin and are then left to cool to 50° C.

An 87% glycerol solution containing 0.5% carbohydrase heated beforehand to 50° C. is then sprayed onto the grapes thus pretreated. The grapes are then spread over an aluminium foil and placed in an oven at 50° C. where they are left to incubate for 3 hours. During this 3 hour incubation period, the spraying step is repeated twice. After the incubation period, the grapes are steeped for 30 minutes in an 87% glycerol solution heated beforehand to 95° C. to inactivate the enzymes and are then rapidly rinsed with water to remove the glycerol present at their surface in order to facilitate their subsequent handling by minimizing the risks of adhesion and agglomeration. The grapes thus treated are then dried in a ventilated oven at 40° C. for about 15 hours with occasional turning. The dry grapes thus obtained have a dry matter content of 88–90%, a water activity of 0.29–0.32 and a glycerol content of 18.5%.

Example 4

Two batches of a product of the muesli type are prepared by mixing 90% base consisting of cereal flakes (wheat, corn, ...) and 10% dry grapes. The first batch A contains standard commercially available grapes while the second batch B contains grapes prepared in accordance with Example 3 containing 15.3% glycerol.

The two batches are stored at 30° C.

Samples are taken after storage for 1 month and 3 months. The base and the grapes are separated and the dry matter content (DM), the water activity value (Aw) and the hardness of the base and the grapes are determined. Hardness is evaluated by sampling and awarding marks on a scale of 1 (very hard) to 5 (very tender).

The following results are obtained:

| Storage time | Batch A Base | Batch A Grapes | Batch B Base | Batch B Grapes |
| --- | --- | --- | --- | --- |
| t = 0 | | | | |
| DM (%) | 4.4 | 15.5 | 4.4 | 17.2 |
| Aw | 0.22 | 0.59 | 0.22 | 0.46 |
| t = 1 month | | | | |
| DM (%) | 5.5 | 7.4 | 4.8 | 12.1 |
| Aw | 0.32 | 0.34 | 0.30 | 0.30 |
| Hardness | — | 1.3 | — | 4.0 |
| t = 3 months | | | | |
| DM (%) | 5.0 | 7.2 | 5.0 | 8.3 |
| Aw | 0.36 | 0.36 | 0.31 | 0.31 |
| Hardness | — | 2.3 | — | 3.8 |

It can be seen that, after storage for 1 month or 3 months at 30° C., the grapes according to the invention have retained their tender character while the standard commercially available grapes are hard and considered unacceptable for consumption.

Example 5

Dry grapes are pretreated, treated and dried in exactly the same way as described in Example 3 except that the carbohydrase is replaced by other enzymes: pectinase, cellulase and galactomannanase. The following results are obtained:

| Enzyme used | Final glycerol content (% based on dry matter) |
| --- | --- |
| Carbohydrase | 18.5 |
| Pectinase | 16.0 |
| Cellulase | 14.7 |
| Galactomannanase | 18.7 |

Accordingly, various enzymes may be used to carry out the invention.

Example 6

Dry grapes are pretreated, treated and dried in exactly the same way as described in Example 3 except that the incubation time is varied. For comparison, the same treatment is applied to a control batch using a glycerol solution containing no enzymes. The following results are obtained:

| Incubation | Glycerol content (% based on dry matter) |
| --- | --- |
| Batch with enzyme | |
| . 3 hours, 50° C. | 24.5 |
| . 6 hours, 50° C. | 26.7 |
| . 15 hours, 50° C. | 27.6 |
| Control batch without enzyme | |
| . 3 hours, 50° C. | 19.1 |
| . 6 hours, 50° C. | 23.2 |
| . 15 hours, 50° C. | 16.7 |

It can be seen that the use of enzymes considerably improves the absorption of glycerol by the grapes. It can also be seen that the final glycerol content of the grapes can be influenced through the incubation time.

We claim:

1. A process for treating dried fruit comprising:

contacting and incubating dried fruit with a glycerol solution containing a carbohydrase enzyme in an amount of 0.05 to 0.5 parts enzyme by weight per 100 parts fruit, wherein incubation is carried out at a temperature of from 40° C. to 60° C. for a time sufficient so that the fruit absorbs at least 10% by weight glycerol;

inactivating the carbohydrase enzyme; and drying the incubated fruit so that the fruit has a water activity of from 0.25 to 0.40.

2. A process according to claim 1 wherein the dried fruit is steeped in the glycerol solution.

3. A process according to claim 1 wherein the dried fruit is contacted by spraying with the glycerol solution and then incubated.

4. A process according to claim 3 further comprising spraying the dried fruit during incubation.

5. A process according to claim 1 wherein the glycerol solution is pure glycerol.

6. A process according to claim 1 wherein the glycerol solution is an aqueous solution containing 80% to 90% glycerol.

7. A process according to claim 1 wherein the dried fruit is incubated for from 2 hours to 5 hours.

8. A process according to claim 1 wherein one part by weight dried fruit is contacted and incubated with one to two parts by weight glycerol solution.

9. A process according to claim 1 further comprising, prior to to contacting and incubating the dried fruit with the glycerol solution, immersing the fruit in water at a temperature of from 90° C. to 100° C. for from 2 minutes to 4 minutes.

10. A process according to claim 1 wherein the enzyme is inactivated by steeping the incubated fruit in a glycerol solution at a temperature of from 75° C. to 95° C. for from 20 minutes to 40 minutes.

11. A process according to claim 1 wherein the dried fruit is dried to a dry matter content of from 88% to 92%.

12. A process according to claim 1 further comprising rinsing the dried fruit with water before drying the dried fruit.

13. A process according to claim 1 wherein the enzyme is pectinase.

14. A process according to claim 1 wherein the enzyme is cellulase.

15. A process according to claim 1 wherein the enzyme is galactomannanase.

* * * * *

UNITED STATES PATENT AND TRADEMARK OFFICE
CERTIFICATE OF CORRECTION

PATENT NO. : 5,362,503
DATED : November 8, 1994
INVENTOR(S) : Josef BURRI

It is certified that error appears in the above-indentified patent and that said Letters Patent is hereby corrected as shown below:

Column 6, line 10, claim 9, delete the second occurrence of "to".

Signed and Sealed this

Seventeenth Day of January, 1995

Attest:

BRUCE LEHMAN

Attesting Officer

Commissioner of Patents and Trademarks